United States Patent [19]
Affolter

[11] Patent Number: 5,079,001
[45] Date of Patent: Jan. 7, 1992

[54] LIQUID ORAL FORMULATION OF DICLOFENAC

[75] Inventor: Heidi Affolter, Birsfelden, Switzerland

[73] Assignee: Ciba-Geigy Corporation, Ardsley, N.Y.

[21] Appl. No.: 518,699

[22] Filed: May 3, 1990

Related U.S. Application Data

[63] Continuation-in-part of Ser. No. 431,369, Nov. 3, 1989, abandoned.

[51] Int. Cl.$^5$ ................................................ A61K 9/10
[52] U.S. Cl. .................................... 514/567; 424/83; 424/455; 514/825; 514/937
[58] Field of Search .................... 424/400, 455, 83; 514/553, 567, 937

[56] References Cited

U.S. PATENT DOCUMENTS

| | | | |
|---|---|---|---|
| 3,558,690 | 1/1971 | Sallmann et al. | 260/471 |
| 4,968,505 | 11/1990 | Okada et al. | 424/400 |

FOREIGN PATENT DOCUMENTS

| | | |
|---|---|---|
| 2315948 | 1/1977 | France . |
| 1550139 | 8/1979 | United Kingdom . |
| 2134529 | 8/1984 | United Kingdom . |

OTHER PUBLICATIONS

Derwent Abstract 27,248.
Derwent Abstract 85-051,062.
Chem. Abstr. vol. 99: 93,582y.
Chem. Abstract, vol. 102:50,791d.
Chem. Abstract, vol. 225,919f.
Chem. Abstract, vol. 103:59,148c.
Clin. Pharmacol. Ther. 23:414–420 (1978).
J. Chromatogr. Biomed. Appl. 383:412–418 (1986).
Pharm. Ztg. 129:2387-2392 (1984).
Arch. Pharm. Chemi. Sci. Ed. 8:100-108(3), 1980.
Minerva Ortop. (Italy), 1977, 28/6 (349–358).
Clin. Trials (UK), 1986, 23/6 (382–393).
Invest. Med. Int. (Mexico), 1986, 13/1, (50–55).
Jpn. J. Ophthamol. (Japan), 1983, 27/3, (535, 542).
TherapieWoche (Germany, West), 1983, 33/19 (2619–2625).

*Primary Examiner*—Thurman K. Page
*Assistant Examiner*—James M. Spear
*Attorney, Agent, or Firm*—Irving M. Fishman

[57] ABSTRACT

The invention relates to an aqueous oral pharmaceutical preparation of diclofenac which can be used for treating pain and inflammatory processes, and to the preparation of a preparation of this type.

21 Claims, No Drawings

LIQUID ORAL FORMULATION OF DICLOFENAC

The invention relates to an aqueous oral pharmaceutical preparation of diclofenac, and to its use and preparation.

Diclofenac, chemical name o-(2,6-dichloroanilino)-phenylacetic acid, is known as a potent analgesic and antirheumatic and is described, for example, in U.S. Pat. No. 3,558,690.

Much effort has been directed toward developing for this active ingredient an aqueous, individually dosable oral form of administration which has a neutral or pleasant taste and, in addition, has a satisfactory shelf life so as to make available to doctors and patients an appropriate alternative to other oral preparations.

It is known that diclofenac has a bitter taste and causes a scratching sensation in the throat. In addition, it has proven disadvantageous that, when customary aqueous oral solutions are used, water-insoluble hydrates are formed which result in precipitations. It is furthermore known that diclofenac cyclizes, in particular in acid solution, to form 1-(2,6dichlorophenyl)indolin-2-one. Thus, corresponding aqueous pharmaceutical formulations of diclofenac do not have an adequate shelf life and, as a consequence, would not meet the criteria for registration as a medicament.

The present invention had the object of developing an aqueous oral pharmaceutical preparation of diclofenac which does not have the disadvantages mentioned.

This object is achieved by the preparation according to the invention. This has the features that a pH range is selected in which the active ingredient has the lowest water solubility and that diclofenac is in suspended form.

Surprisingly, when aqueous formulations of this type are used, absolutely no prohibitive formation of indolinone, in particular, is observed. In addition, preparations of this type have a pleasant taste and do not cause a scratching sensation in the throat.

The preferred active ingredient concentration of the preparation according to the invention is about 0.4 or 0.5, respectively, to about 10% by weight, in particular about 0.45 to about 5% by weight, especially about 0,5 to about 4%, primarily about 0,5 to about 2% by weight, especially preferred concentrations are about 0,5%, 1%, 2% or 4% by weight.

The pH range according to the invention is, in particular, between about 2 and about 3.5, preferably between about 2.5 and about 3,5, and is established by means of pharmaceutically acceptable acids or buffer systems which are known per se. Suitable pharmaceutically acceptable acids are preferably carboxylic acids, such as acetic acid, malonic acid, fumaric acid, maleic acid, succinic acid, lactic acid, tartaric acid or primarily citric acid. Examples of buffer systems of this type are sodium citrate/HCl or citric acid/phosphate buffer.

Appropriate forms of administration of the suspension drops, mixtures, juices or syrups, which may also be used in dose-unit forms.

The composition according to the invention may contain further pharmaceutically acceptable adjuncts and additives, for example preservatives, antioxidants, fragrances, dyes, sweeteners, suspension stabilizers and/or wetting agents.

Suitable preservatives, which protect against infestation by microorganisms, are benzoic acid or salts thereof, such as sodium, potassium or calciumsalts, 4-hydroxybenzoic acid esters, such as methyl, ethyl or propyl 4-hydroxybenzoate (PHB esters), phenols, such as tert-butyl-4-methoxy- or 2,6-ditert-burtyl-4-methylphenol, phenyl (lower alkanols), benzyl alcohol, 4-chloro- or 2,4-dichlorobenzyl alcohol, 2-phenylethanol or 3-phenylproponanol, chlorohexidine diacetate or digluconate, thiabendazole, furthermore nitrofural, quarternary ammonium halides, such as alkonium bromide, benzalkonium chloride, cetrimonium bromide, phenododecinium bromide or cetylpyridinium chloride, or primarily sorbic acid, for example in a proportion of about 0.01 to about 0.1% by weight.

Suitable antioxidants, which are intended to inhibit oxidative processes, are, for example, sulfites, such as alkali metal sulfites, alkali metal bisulfites or alkali metal pyrosulfites, for example the corresponding sodium or potassium salts, thiodipropionic acid, thioglycolk thiolactic acid, glutathione, but preferably cystein, ascorbic acid and esters thereof, for example ascorbic acid myristate, palmitate or stearate, or esters of gallic acid, such as propyl, octyl or dodecyl esters, for example in a proportion of about 0.01 to about 0.1% by weight. Synergists, such as citric acid, citraconic acid, phosphoric acid or tartaric acid, may be admixed.

To improve the flavor, suitable fragrances are, for example, etherial oils, in particular those derived from fruits, such as oranges, and oils from Seville oranges, mandarines or lemons, and furthermore caramel.

Examples of suitable dyes are Indigo Tin I(blue), Amaranth(red), Yellow orange S (orange), Tartrazine XX (yellow) or chlorophyll (green).

Examples of suitable sweeteners, which are present in high concentration, in for example, syrups, are sugar such as monosaccharides or disaccharides, for example D-glucose, D-fructose, D-xylose, maltose or sucrose, polyols, such as glycerol, dulcitol, mannitol, sorbitol or xylitol, or artificial sweeteners, such as saccharine or the corresponding sodium, potassium or calcium salt, cyclamate or the corresponding sodium or calcium salt, aspartam or acesulfam or the potassium salt thereof, furthermore Dulcin or ammonium glycyrrhizinate.

The suspension stabilizers are intended to ensure that the individual doses removed have a constant active ingredient content. Examples of appropriate stabilizers are inorganic suspension stabilizers, for example colloidal silicates having a high aluminum and magnesium content, such as bentonite, Veegum or Gel White, colloidal silica, for example Aerosil (Degussa), Cabosil (Cabot), organic stabilizers, for example swelling agents, such as alginates, for sodium alginate, calcium alginate or propylene glycol alginate, gum arabic, tragasanth, karaya gum, sterculia gum, carrageen, guar gum or agar, synthetic or semisynthetic swelling agents, for example 1,2-epoxide polymers, in particular ethylene oxide homopolymers having a degree of polymerization of about 2,000–100,000, which are known, for example, under the trade name Polyox (union Carbide), preferably swellable cellulose ethers, for example methyl- or ethyl cellulose, hydroxy ethyl cellulose, hydroxypropyl cellulose, hydroxypropylmethyl cellulose, methyl- or ethylhydroxyethyl cellulose, carboxymethyl cellulose or an alkali metal salt thereof, or microcrystalline cellulose, or water-soluble polyvinyl compounds, such as polyvinyl acetate, polyvinyl alcohol or polyvinylpyrrolidone.

Suspension stabilizers are advantageously present in an amount which ranges up to 2% by weight, preferably about 0,4 to about 1,9% by weight. The stabilizer content may be a combination of the above-mentioned stabilizers.

Wetting agents may advantageously be added to the stabilizers. Examples of suitable wetting agents are sulfosuccinates, such as dihexyl sulfosuccinate, dioctyl sulfosuccinate or diamyl sulfosuccinate, sulfonates or sulfates, for example Na alkylnaphthalene-sulfonates, fatty alcohol sulfonates or fatty alcohol polyglycol ether sulfates, fatty acid polyglycol esters, for example polyethylene glycol stearates, polyglycol esters of $C_8$–$C_{18}$ fatty acids, fatty alcohol polyglycol ethers, for example lauryl, cetyl, stearyl or oleyl alcohol polyglycol ether or cetylstearyl alcohol polyglycol ether, poly(fatty acid) ester polyglycol ethers, for example polyethylene glycol sorbitan monolaurate, monopalmitate, monostearate or monooleate, glycerol fatty acid ester polyglycol ether or pentaerythritol fatty acid polyglycol ether, sucrose esters, for example sucrose monostearate or distearate or sucrose monopalmitate, ethoxylated vegetable oils, for example ethoxylated castor oil or hydrogenated and ethoxylated castor oil, or block polymers, such as polyoxyethylenepolyoxypropylene polymers.

The aqueous oral pharmaceutical preparations of diclofenace according to the invention are prepared, for example, as follows depending on the nature of the form of administration.

Thus, for example, the adjuncts and additives are incorporated into the water with or without warming, for example in a temperature range of from about 20° to about 100° C. The active ingredient is then suspended in this base. However, the sequence of mixing the components of the preparation according to the invention is not important.

To prepare syrups, for example, the suspension agent and the appropriate suspension stabilizer are added to the water. A sweetener and, if desired, preservatives, antioxidants, fragrances and/or dyes are incorporated with or without warming, for example in a temperature range of from about 50° to about 100° C. The active ingredient is then suspended in the medium.

The aqueous oral pharmaceutical preparation according to the invention can be used, for example, for treating pain and inflammatory processes.

The invention also relates, in particular, to the preparations and preparation processes described in the Examples.

The Examples below serve merely to illustrate the above-described invention; however, they are not intended to represent a limitation.

EXAMPLE 1

Syrup containing 1% by weight of diclofenace

| Composition: | |
|---|---|
| Diclofenac (free acid) | 1.00 g |
| Hydroxyethyl cellulose (Natrosol 250 G) | 0.50 g |
| Cellulose and sodium carboxymethyl cellulose (Avicel RC 591) | 1.20 g |
| Sorbitol solution | 25.00 g |
| Sorbic acid | 0.05 g |
| Vitamin C | 0.10 g |
| Citric acid | 0.20 g |
| Saccharine sodium | 0.06 g |
| Demineralized water | 71.89 g |
| | 100.00 g |
| pH: 2.9 | |

PREPARATION

Avicel is suspended in the water using a high-speed mixer, Natrosol is admixed, and the mixture is left to swell for about 1 hour. Sorbitol solution and sorbic acid are added, and the mixture is heated to about 85° with stirring. After the mixture has been cooled to room temperature, Vitamin C, citric acid and saccharine and dissolved consecutively therein with stirring. The active ingredient is suspended in the mixture with the aid of the mixer, and the mixture is subsequently deaerated.

EXAMPLE 2

Syrup containing 1% of diclofenac:

| Diclofenac (free acid) | 1.0 g |
|---|---|
| Sucrose | 40.0 g |
| Agar powder | 0.3 g |
| Sorbic acid | 0.1 g |
| Vitamin C | 0.1 g |
| Citric acid 1 AQ | 0.2 g |
| Disodium phosphate 2 AQ | 0.08 g |
| Lemon aroma | 0.1 g |
| Demineralized water | 58.12 g |
| | 100.00 g |
| pH: 3.2 | |

PREPARATION

The water is warmed to about 90° C. and sorbic acid is dissolved therein. Agar powder is subsequently scattered into the mixture and dispersed using a high-speed mixer. The mixture is then left to swell at 90° C. for about 30 minutes. The sucrose is added and dissolved with stirring. After the mixture has cooled to about 40° C., citric acid, disodium phosphate and Vitamin C are added consecutively and dissolved. After the fragrance has been added, the active ingredient is ground with a small amount of the base and then distributed in the remainder of the base.

EXAMPLE 3

Mixture containing 1% of diclofenac

| Diclofenac (free acid) | 1.0 g |
|---|---|
| Hydroxyethyl cellulose (Natrosol 250 G) | 0.5 g |
| Cellulose and sodium carboxymethyl cellulose (Avicel RC 591) | 1.2 g |
| Sorbic acid | 0.1 g |
| Vitamin C | 0.1 g |
| Citric acid 1 AQ | 0.2 g |
| Saccharine sodium | 0.06 g |
| Disodium phosphate 2 AQ | 0.08 g |
| Lemon aroma | 0.1 g |
| Demineralized water | 97.16 g |
| | 100.00 g |
| pH: 3.2 | |

PREPARATION

Avicel is dispersed in 50 g of water using a high-speed mixer, Natrosol is admixed, and the mixture is left to swell for about 1 hour. The remainder of the water (47.16 g) is heated to about 60° C. and sorbic acid is dissolved therein. After the latter mixture has cooled to 40° C., saccharin, citric acid, disodium phosphate and Vitamin C are added consecutively and dissolved. This solution is mixed with the A vicel dispersion. After the fragrance has been added, the active ingredient is ground with a small amount of the base and then distributed in the remainder of the base.

EXAMPLE 4

Drops containing 1% of diclofenac:

| | |
|---|---|
| Diclofenac (free acid) | 1.0 g |
| Meyprogat 150 (guar gum) | 0.5 g |
| Sorbitol solution | 50.0 g |
| Sorbic acid | 0.1 g |
| Vitamin C | 0.1 g |
| Citric acid 1 AQ | 0.2 g |
| Disodium phosphate 1 AQ | 0.08 g |
| Lemon aroma | 0.1 g |
| Demineralized water | 47.92 g |
| | 100.00 g |
| | pH: 3.1 |

PREPARATION

The water is warmed to about 90° C. and sorbic acid is dissolved therein. Meyprogat is scattered into the mixture and dispersed using a high-speed mixer. The mixture is then left to swell at 90° C. for about 30 minutes. Sorbitol solution is then added. After the mixture has cooled to about 40° C., citric acid, disodium phosphate and Vitamin C are added consecutively and dissolved with stirring. After the fragrance has been added, the active ingredient is ground with a small amount of the base and then distributed in the remainder of the base.

EXAMPLE 5 syrup containing 1% by weight of diclofenac

| | |
|---|---|
| Diclofenac (free acid) | 1.00 g |
| Hydroxyethyl cellulose (Natrosol 250 G) | 0.50 g |
| Cellulose and sodium carboxymethyl cellulose (Avicel RC 591) | 1.20 g |
| Sorbitol solution | 25.00 g |
| Sorbic acid | 0.05 g |
| Vitamin C | 0.60 g |
| Citric acid | 1.00 g |
| Saccharine sodium | 0.06 g |
| Demineralized water | 70.59 g |
| | 100.00 g |
| | pH: 2.3 |

PREPARATION

Avicel is suspended in the water using a high-speed mixer. Natrosol is admixed and the mixture is left to swell for about 1 hour. Sorbitol solution and sorbic acid are added, and the mixture is heated to about 85° with stirring. After the mixture has cooled to room temperature, Vitamin C, citric acid and saccharine are dissolved consecutively therein with stirring. The active ingredient is then suspended therein using the mixer, and the mixture is subsequently deaerated.

EXAMPLE 6

Syrup containing 1% by weight of diclofenac

| | |
|---|---|
| Diclofenac (free acid) | 1.00 g |
| Hydroxyethyl cellulose (Natrosol 250 G) | 0.50 g |
| Cellulose and sodium carboxymethyl cellulose (Avicel RC 591) | 1.20 g |
| Sorbitol solution | 25.00 g |
| Vitamin C | 0.60 g |
| Citric acid | 1.00 g |
| Methylparaben | 0.12 g |
| Propylparaben | 0.05 g |
| Saccharine sodium | 0.06 g |
| Demineralized water | 70.49 g |
| | 100.00 g |
| | pH: 3.0 |

PREPARATION

Avicel is suspended in the water using a high-speed mixer, Natrosol is admixed, and the mixture is left to swell for about 1 hour. Sorbitol solution and sorbic acid are added, and the mixture is heated to about 85° with stirring. After the mixture has cooled to room temperature, Vitamin C, citric acid and saccharine are dissolved consecutively therein with stirring. The active ingredient is suspended therein using the mixer, and the mixture is subsequently deaerated.

EXAMPLE 7

Syrup containing 4% by weight of diclofenac

| | |
|---|---|
| Diclofenac (free acid) | 4.000 g |
| Aroma golden Syrup (52.927/A) | 0.006 g |
| Cellulose and sodium carboxymethyl cellulose (Avicel RC 591) | 1.200 g |
| Banana aroma (54.330/A) | 0.013 g |
| Citric acid (1AQ) | 1.000 g |
| Hydroxyethyl cellulose (300 mPas) | 0.500 g |
| Saccharine sodium (cryst.) | 0.060 g |
| Sorbic acid | 0.100 g |
| Sorbitol solution | 25.000 g |
| Vitamin C | 0.600 g |
| Water (deionized) | 75.521 g |
| | 108.000 g |
| | (= 100 ml) |
| pH = 2.3 | |

PREPARATION

Avicel is suspended in the water using a high-speed mixer, Natrosol is admixed, and the mixture is left to swell for about 1 hour. Sorbitol solution and sorbic acid are added, and the mixture is heated to about 85° with stirring. After the mixture has cooled to room temperature, Vitamin C, citric acid and aspartame are dissolved consecutively therein with stirring. The active ingredient is suspended therein using the mixer, and the mixture is subsequently deaerated.

EXAMPLE 8

Syrup containing 0.5% by weight of diclofenac

| | |
|---|---|
| Diclofenac (free acid) | 0.500 g |
| Aroma golden Syrup (52.927/A) | 0.006 g |
| Cellulose and sodium carboxymethyl cellulose (Avicel RC 591) | 1.200 g |
| Banana aroma (54.330/A) | 0.013 g |
| Citric acid (1AQ) | 1.000 g |
| Hydroxyethyl cellulose (300 mPas) | 0.500 g |
| Aspartame | 0.150 g |
| Sorbic acid | 0.100 g |
| Sorbitol solution | 25.000 g |
| Vitamin C | 0.600 g |

| | |
|---|---|
| -continued | |
| Water (deionized) | 70.931 g |
| | 100.000 g |

PREPARATION

Avicel is suspended in the water using a high-speed mixer, Natrosol is admixed, and the mixture is left to swell for about 1 hour. Sorbitol solution and sorbic acid are added, and the mixture is heated to about 85° with stirring. After the mixture has cooled to room temperature, Vitamin C, citric acid and aspartame are dissolved consecutively therein with stirring. The active ingredient is suspended therein using the mixer, and the mixture is subsequently deaerated.

What is claimed is:

1. An aqueous oral pharmaceutical preparation comprising about 0.4% to about 10% by weight diclofenac is suspended form, said preparation having a pH selected from the range of between about 2 to about 3.5 wherein said pH is established by a pharmaceutically acceptable acid or buffer system and which contains a pharmaceutically acceptable adjunct or additive selected from the group consisting of preservatives, antioxidants, fragrances, dyes, sweeteners, suspension agents, and wetting agents.

2. A preparation according to claim 1, wherein the active ingredient concentration is about 0.5 to about 2% by weight.

3. A preparation according to claim 1, wherein the pH is set using citric acid.

4. A preparation according to claim 1, wherein the pH is set using citric acid/phosphate buffer.

5. A preparation according to claim 1, which contains, as preservative, benzoic acid or salts thereof, 4-hydroxybenzoid acid esters, phenols, phenyl (lower alkanols), quarternary ammonium halides or sorbic acid.

6. A preparation according to claim 1, which contains sorbic acid.

7. A preparation according to claim 1, which contains, as antioxidants, cystein, ascorbic acid or esters thereof, or an ester of gallic acid.

8. A preparation according to claim 1, which contains ascorbic acid.

9. A preparation according to claim 1, which contains, as sweetener, a monosaccharide, disaccharide, polyol or artificial sweetener.

10. A preparation according to claim 1, which contains, as sweetener, saccharin, cyclamate, aspartame, a sugar alcohol or a mono- or di-saccharide.

11. A preparation according to claim 1, which contains, as suspension stabilizer, colloidal silicates having a high aluminum and magnesium content, colloidal silica, swelling agnes, swellable cellulose ethers, carboxymethylcellulose or an alkali metal salts thereof, microcrystalline cellulose or water-soluble polyvinyl compounds.

12. A preparation according to claim 1, which contains hydroxyethylcellulose and/or cellulose and sodium carboxymethylcellulose or agar or guar gum.

13. A preparation according to claim 1 in the form of drops, mixture, juice or syrup.

14. A preparation according to claim 1 in dose-unit form.

15. A method for the treatment of pain and inflammatory conditions comprising administering a pharmaceutical preparation according to claim 1 to a warm-blooded organism in need of such.

16. The preparation of claim 1 wherein said diclofenac is present in an amount of about 0.5 to about 10% by weight.

17. The preparation of claim 1 wherein said diclofenac is present in an amount of about 0.45 to about 5% by weight.

18. The preparation of claim 1 further comprising a suspension stabilizer selected from a colloidal silicate having a high aluminum and magnesium content, an alginate, an ethylene homopolymer having a degree of polymerization of about 2,000–1,000,000, a swellable cellulose ether, microcrystalline cellulose, and a water-soluble polyvinyl compound.

19. The preparation of claim 18 wherein said stabilizer is present in an amount of about 0.4 to about 1.9% by weight.

20. The preparation of claim 1 further comprising a hydroxyethylcellulose, cellulose, sodium carboxymethyl cellulose, citric acid, sorbic acid, ascorbic acid, and soribtol.

21. A method for stabilizing diclofenac in an aqueous medium in a concentration range of about 0.4% to about 10% by weight diclofenac, comprising suspending said diclofenac in water and adjusting the pH to a pH selected from the range of between about 2 to about 3.5 wherein said pH is established by a pharmaceutically acceptable acid or buffer system and which contains a pharmaceutically acceptable adjunct or additive selected from the group consisting of preservatives, antioxidants, fragrances, dyes, sweeteners, suspension agents and wetting agents.

* * * * *